United States Patent
Shoji et al.

(10) Patent No.: US 6,668,616 B1
(45) Date of Patent: Dec. 30, 2003

(54) CARBON MONOXIDE SENSOR

(75) Inventors: Rihito Shoji, Osaka (JP); Nobuharu Katsuki, Kyoto (JP); Takashi Ida, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/857,026

(22) Filed: Aug. 9, 2001

(30) Foreign Application Priority Data

Oct. 1, 1995 (JP) .......................................... 11-281305
May 24, 2000 (JP) ...................................... 2000-152385

(51) Int. Cl.[7] .......................................... G01N 27/416
(52) U.S. Cl. ...................... 73/23.2; 73/23.31; 73/31.05; 204/421; 204/424
(58) Field of Search ............................. 73/23.2, 23.31, 73/31.05; 204/421, 424, 425, 426

(56) References Cited

U.S. PATENT DOCUMENTS

| 4,025,412 | A | * | 5/1977 | LaConti ........................ 204/426 |
| 4,582,657 | A | * | 4/1986 | Shibata et al. ............... 204/426 |
| 4,664,757 | A | | 5/1987 | Zupancic et al. |
| 5,302,274 | A | | 4/1994 | Tomantschger et al. |
| 5,573,648 | A | | 11/1996 | Shen et al. ................... 204/426 |
| 5,897,766 | A | * | 4/1999 | Kawatsu ....................... 204/426 |

FOREIGN PATENT DOCUMENTS

| EP | 0 431 565 | 6/1991 | |
| EP | 0 710 835 | 5/1996 | .................. 204/426 |
| EP | 0 911 629 | 4/1999 | .................. 204/426 |
| JP | 8-29390 | 2/1996 | |
| JP | 8-327590 | * 12/1996 | .................. 204/426 |
| JP | 11-219716 | * 8/1999 | .................. 204/426 |

OTHER PUBLICATIONS

Patent Abstracts of Japan, vol. 015, No. 487 (p–1286), Dec. 10, 1991 & Jp 03–211454 A (Matsushita Electric Ind. Co., Ltd.), Sep. 17, 1991 * abstract *.

* cited by examiner

Primary Examiner—Daniel S. Larkin
(74) Attorney, Agent, or Firm—Wenderoth, Lind & Ponack, L.L.P.

(57) ABSTRACT

A carbon monoxide sensor having a fast response performance without leakage of object gas to an exterior atmosphere is presented. The sensor includes: a proton conductive electrolyte film; two electrodes having catalysts and being disposed at opposite sides of the proton conductive electrolyte film; a positive electrode current collector plate, where a gas passage having a gas inlet and outlet is formed, with the gas passage contacting one of electrodes; a negative electrode current collector plate having plural holes contacting the other of the electrodes; a direct-current power source having positive and negative terminals connected to the positive and negative electrode current collector plates, respectively; and a current detecting unit for detecting a current that varies depending on a concentration of carbon monoxide in an object gas, containing hydrogen, flowing in the gas passage.

34 Claims, 14 Drawing Sheets

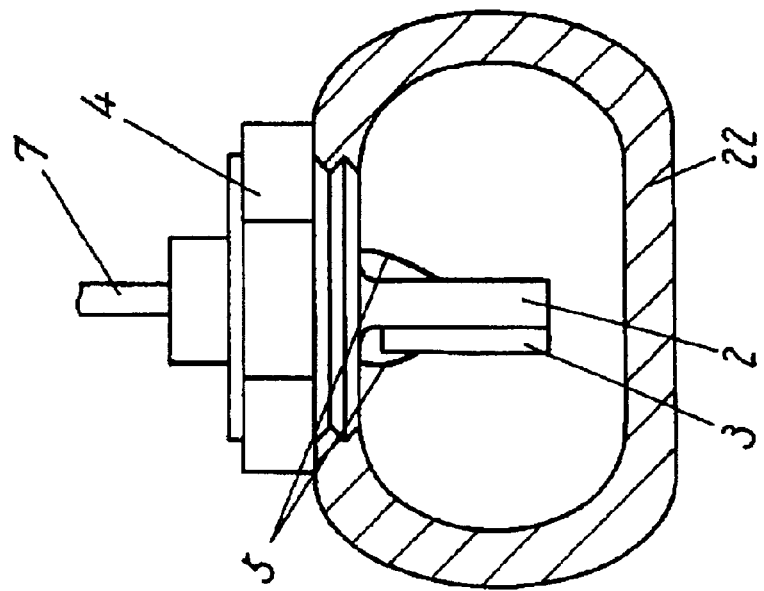
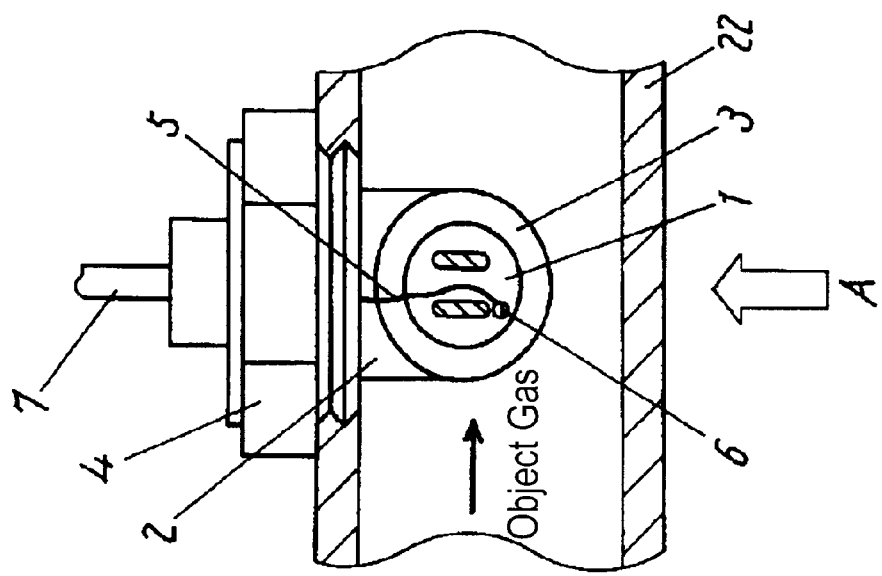
Fig. 1A
Fig. 1B

CARBON MONOXIDE SENSOR

TECHNICAL FIELD

The present invention relates to a carbon monoxide sensor for detecting the a concentration of carbon monoxide in fuel gas having a high content of hydrogen used, for example, in a fuel cell.

BACKGROUND ART

Recently, a fuel cell using a solid high polymer proton conductive film is intensively developed for a home appliance and an automobile. The fuel cell uses hydrogen gas as fuel gas for operation, and hence requires a reformer for producing hydrogen gas by reforming liquid fuel such as methanol or utility gas. However, a fuel gas mainly composed of hydrogen produced by the reformer contains very little carbon monoxide of about scores of ppm. Carbon monoxide which is adsorbed in a platinum catalyst composing electrodes of the fuel cell (this phenomenon is called poisoning) lowers an electromotive force of the fuel cell. Consequently, it is necessary to monitor concentration of carbon monoxide in the fuel gas and to control the fuel cell accordingly.

A carbon monoxide sensor for detecting carbon monoxide in fuel gas for a fuel cell has been disclosed, for example, in Japanese Laid-open Patent No. 8-327590.

A sectional view of a schematic structure of this carbon monoxide sensor is shown in FIG. 13. An electrolyte film 110 is composed of a high polymer having proton conductivity. On both surfaces of the film, electrodes 112, 114 having a carbon cloth containing kneaded carbon powder and a platinum catalyst carried thereon are bonded by performing hot pressing. Mesh metal plates 116, 118 are disposed on surfaces of the electrodes 112, 114, on which the electrolyte film 110 is not disposed, respectively. The electrolyte film 110, electrodes 112, 114, and metal plates 116, 118 are held by flanges 120a, 122a provided inside of metal cylindrical holders 120, 122. An o-ring 126 for sealing gas is disposed at an electrolyte film 110 side at an end of the holder 122.

On an outer circumference of the holders 120, 122, threaded portions 120b, 122b are formed. The holders 120, 122 are fixed by being driven into threaded portions 124a, 124b formed inside of an insulating member 124 made of polytetrafluoroethylene, such as TEFLON (a trademark of Du Pont).

At one end of the holder 120, one end of a gas influent passage 128 is connected, from which object gas (fuel gas in this case) is introduced into the carbon monoxide sensor. One end of the holder 122 is not connected to the gas influent passage 128 and opens to an atmosphere.

Another end of the gas influent passage 128 is connected to a branch port 140a, provided at a part of a fuel gas passage 140, to allow gas to be introduced into the fuel cell.

Detecting terminals 120T, 122T are provided at the holders 120, 122, and an electric circuit 130 is connected to these terminals. The electric circuit 130 is composed of a voltmeter 132, and a resistor 134, for adjusting the load current, connected in parallel with the voltmeter. The detecting terminals 120T and 122T are connected to negative and positive electrodes, respectively.

An operation of the carbon monoxide sensor will be explained. An object gas (fuel gas) containing much hydrogen gas reaches the electrode 112 through the gas influent passage 128. The electrode 114 always contacts oxygen gas in the atmosphere. Therefore, on a surface of the electrolyte film 110 contacting the electrodes 112,114, hydrogen gas and oxygen gas react similarly to that as in the fuel cell to generate an electromotive force between the electrodes 112 and 114. The resistor 134 connected between the electrodes 112 and 114 creates a specified load current flow, and the voltmeter 132 detects a voltage between the electrodes 112 and 114.

In this situation, if carbon monoxide is mixed in the object gas, the carbon monoxide is adsorbed into the platinum catalyst at the electrode 112 and poisons the electrode 112. As a result, hydrogen gas and oxygen gas are prevented from reacting and voltage between the electrodes 112 and 114 is lowered. Since concentration of carbon monoxide relates to a degree of poisoning, by measuring voltage between the electrodes 112 and 114, a concentration of carbon monoxide in the object gas can be detected.

In this carbon monoxide sensor, to the extremely thin electrolyte film 110 made of high polymer sealing the object gas from the atmosphere, a differential pressure between object gas and atmosphere (usually several atmospheres) is always applied. In such circumstance, an abnormally high pressure, or an unexpected large pressure due to vibration or the like, is applied, especially at a portion designated by the circle in FIG. 13. This pressure may breaks the electrolyte film 110, and object gas with a high content of hydrogen gas may leak out to the atmosphere. To avoid such breakage, provided is a structure having a safety valve for releasing object gas in case of abnormal pressure. In any case, leakage of object gas into the atmosphere cannot be avoided.

Japanese Patent Laid-open No.11-219716 discloses another carbon monoxide sensor for detecting carbon monoxide in fuel gas containing much hydrogen gas supplied in a fuel cell.

A perspective exploded view of a schematic structure of this carbon monoxide sensor is shown in FIG. 14. An electrolyte film 50 is an electron exchange film composed of a high polymer having proton conductivity, for example, NAFION (a trademark of Du Pont). On opposite sides of the film, an anode 42 and cathode 44 containing catalyst particles are disposed. Conductive diffusion portions 43 and 45 made of carbon paper contact the anode 42 and cathode 44, respectively. The conductive diffusion portion 43 contacts a housing 54 having an object gas inlet 59, an anode flow channel 46 in which an object gas flows, and an object gas outlet 51. The cathode 44 is exposed to ambient air through an opening 52 of the housing 54. A metal current collector plate 49 in which a plurality of holes are formed contacts the conductive diffusion portion 45 and transfers current to a terminal 47. The terminal 47 projects outwardly from the housing 54 through a slot 55.

An operation of the carbon monoxide sensor will be explained. An object gas (fuel gas) having much hydrogen gas reaches the anode flow channel 46 through the object gas inlet 59. From here, the gas passes through the conductive diffusion portion 43 and is exhausted from the outlet 51. The cathode 44 always contacts oxygen gas in an atmosphere. Therefore, on a surface of the electrolyte film 50 contacting the anode 42 and cathode 44, hydrogen gas and oxygen gas chemically react, similarly to how they react in the fuel cell, so as to generate electricity by using hydrogen gas and oxygen gas, and thereby generates an electromotive force between the anode 42 and cathode 44. Current and voltage at this time are detected by a current detecting device and a voltage detecting device (not shown) connected between the terminal 47 and housing 54.

In this situation, if carbon monoxide is mixed in the object gas, the carbon monoxide is adsorbed into catalyst particles in the anode 42, and hence poisons the anode 42. As a result, hydrogen gas and oxygen gas are prevented from reacting, and the electromotive force between the anode 42 and cathode 44 is lowered. Since concentration of carbon monoxide varies depending on a degree of poisoning, by measuring a current change or voltage change due to drop of an electromotive force, a concentration of carbon monoxide in the object gas can be detected.

A resultant measurement of an output characteristic of the carbon monoxide sensor is indicated with a broken line in FIG. 10. It takes several minutes from introducing object gasp containing 50 ppm of carbon monoxide, into the carbon monoxide sensor for sensor output or electromotive force to change. During this period, voltage or current from the carbon monoxide sensor does not change, and therefore voltage change or current change cannot be measured. Thus, a concentration of carbon monoxide cannot be detected.

SUMMARY OF THE INVENTION

The invention presents a carbon monoxide sensor that includes:
 (i) a proton conductive electrolyte film;
 (ii) a detector composed of electrodes having catalysts disposed at opposite sides of the electrolyte film, and to be disposed in object gas containing hydrogen gas;
 (iii) a power source having positive and negative terminals; and
 (iv) a current detecting unit for detecting a current generated in the detector depending on the concentration of carbon monoxide in the object gas.

In this carbon monoxide sensor, the object gas does not leak to an exterior atmosphere.

A carbon monoxide sensor having a short response time is also presented which includes:
 (i) a proton conductive electrolyte film;
 (ii) an electrode having catalysts disposed at opposite sides of the proton conductive electrolyte film;
 (iii) a positive electrode current collector plate including a gas passage having a gas inlet and outlet, and disposed so that the gas passage may contact one surface of the electrode;
 (iv) a negative electrode current collector plate having a plurality of holes disposed so as to contact another surface of the electrode;
 (v) a direct-current power source having positive and negative terminals connected to the positive electrode current collector plate, and negative electrode current collector plate, respectively; and
 (vi) A current detecting unit for detecting a current that varies depending on a concentration of carbon monoxide in an object gas, that includes hydrogen, flowing in the gas passage.

BRIEF DESCRIPTION OF THE DRAWINGS

FIG. 1A is a schematic front sectional view of a carbon monoxide sensor according to Exemplary Embodiment 1 of the present invention;

FIG. 1B is a side sectional view of the carbon monoxide sensor according to Exemplary Embodiment 1 of the invention;

DETAILED DESCRIPTION OF THE PREFERRED EMBODIMENTS

Embodiments of the invention will be explained below by referring to FIG. 1A to FIG. 12.

Exemplary Embodiment 1

Figure 2:
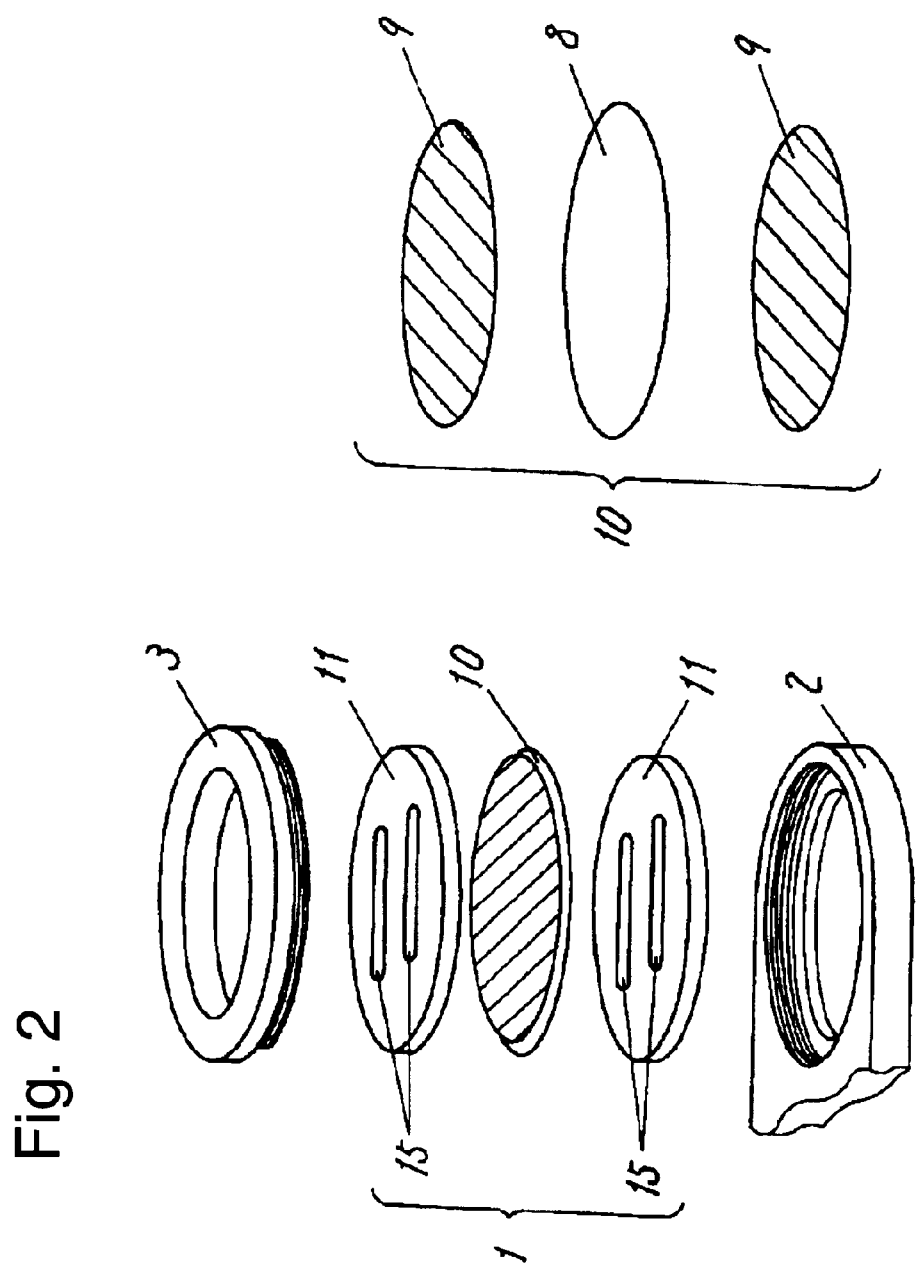
FIG. 2 is a perspective exploded view of a detector of the carbon monoxide sensor according to Exemplary Embodiment 1 of the invention.
Figure 3:
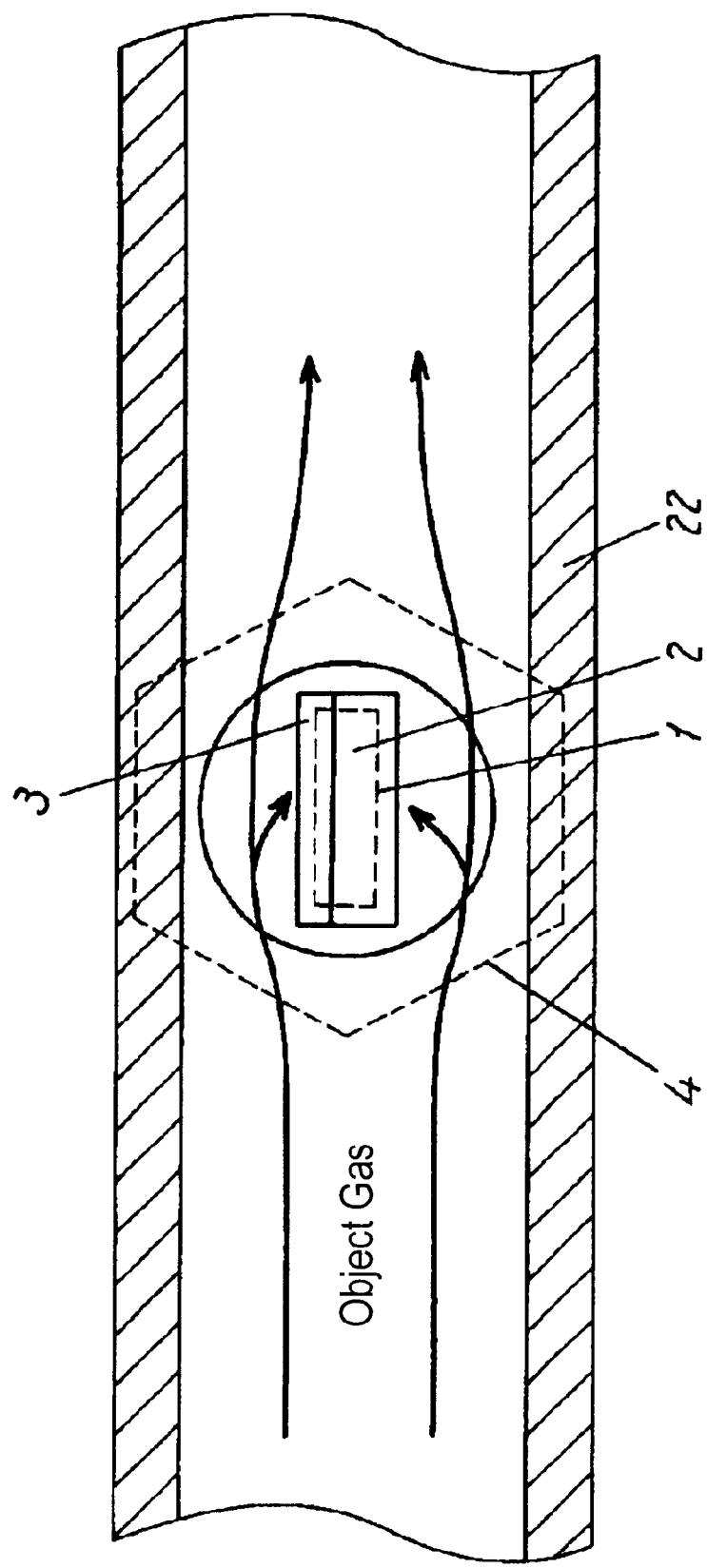
FIG. 3 is a sectional view of the detector of the carbon monoxide sensor according to Exemplary Embodiment 1 of the invention.
Figure 4:
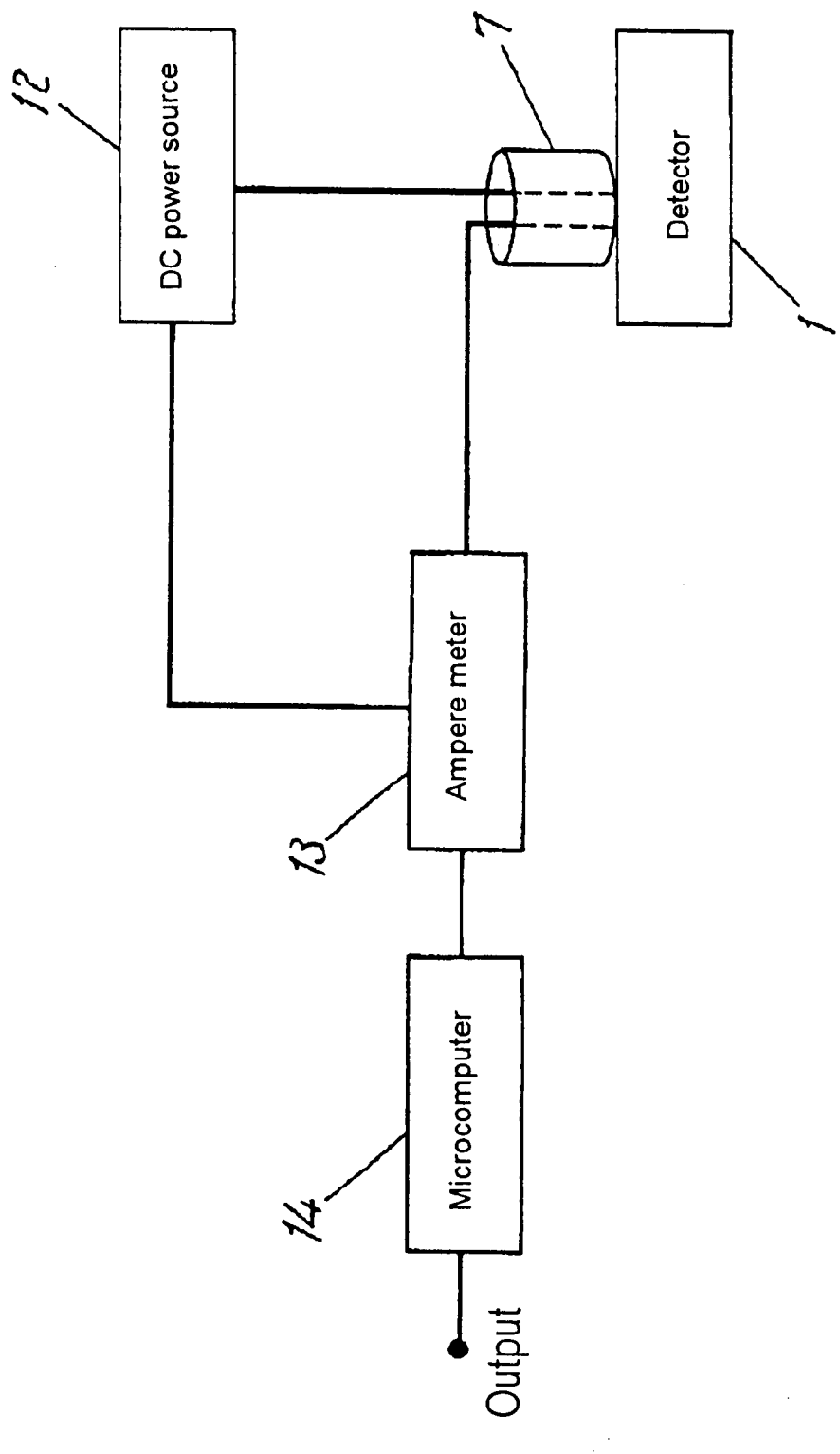
FIG. 4 is a block diagram of a detecting circuit of the carbon monoxide sensor according to Exemplary Embodiment 1 of the invention.
Figure 5:
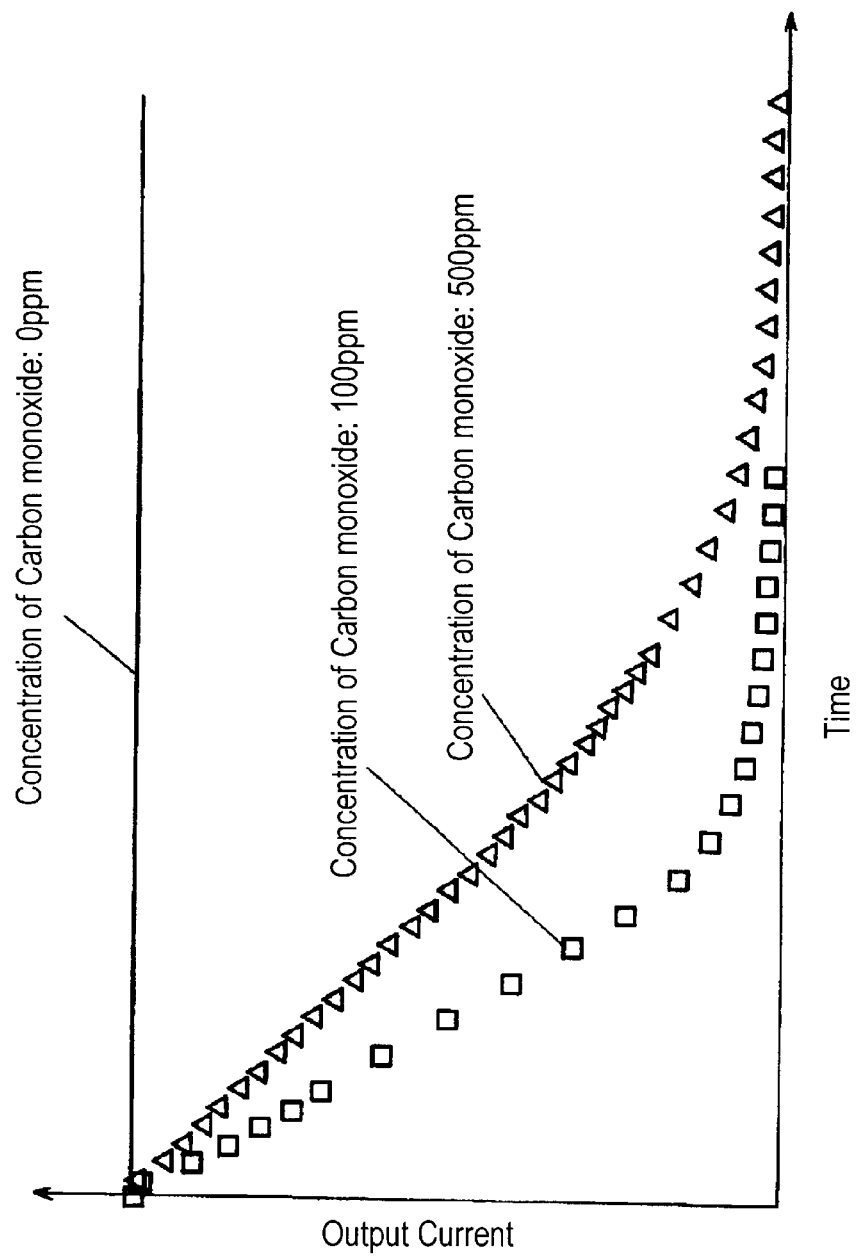
FIG. 5 is an output current characteristic diagram of the carbon monoxide sensor according to Exemplary Embodiment 1 of the invention.

FIG. 1A and FIG. 1B are a schematic front sectional view and a side sectional view of a carbon monoxide sensor 1 according to Exemplary Embodiment 1 of the present invention. FIG. 2 is a perspective exploded view for explaining structure of a detector thereof. FIG. 3 is a sectional view explaining flow of object gas near the detector disposed in a pipe. FIG. 4 is a block diagram of a detecting circuit. FIG. 5 is an output current characteristic diagram of the carbon monoxide sensor.

In FIGS. 1A and 1B, a detector 1 detects concentration of carbon monoxide in an object gas. The detector 1 is fixed with a holder 2 made of insulating polytetrafluoroethylene, for example, TELFON (a trademark of Du Pont), and a ring 3. A part of the holder 2 is inserted and fixed in a mounting threaded portion 4 made of stainless steel (for example, SUS303 in the JIS standard). The mounting threaded portion 4 is driven and fixed in an object gas pipe 22 of a fuel cell through an o-ring (not shown). FIG. 1A and FIG. 1B show only the object gas pipe 22, which is cut off. The detector 1 is fixed in parallel the flow of the object gas. At both sides of the detector 1, a polytetrafluoroethylene-coated output lead wire 5 is connected to junction 6. Each output lead wire 5 is connected to an output cable 7 leading to an external detecting circuit.

In FIG. 2, at both sides of a proton conductive electrolyte film 8 having a diameter of 1.4 cm and made of fluorine high polymer material, two first electrodes 9 are disposed. In the film 8, a platinum catalyst and carbon powder applied on a carbon cloth having a diameter of 1 cm are affixed with a fluorine high polymer material. The electrolyte film 8 held by the two first electrodes 9 is affixed by a hot press at a temperature of 130° C. In order to prevent the two first electrodes 9 from partial short-circuiting due to slight position deviation during operation of the hot press, a diameter of the electrolyte film 8 is larger than a diameter of the first electrodes 9.

At both sides of a detecting element 10 including the electrolyte film 8 and two first electrodes 9, provided are two second electrodes 11 each having a disk shape of a diameter of 1.3 cm and a thickness of 1 mm and made of stainless steel (for example, SUS303 of the JIS standard). Each electrode 11 has two slender penetration holes 15 disposed therein. A surface of the each second electrodes 11 is smoothly processed to have an average roughness of 1.6 μm or less, and a gold plating layer having a thickness of 1 μm is formed thereon. A shape and size of the penetration holes 15 are not particularly specified so long as the object gas can pass therethrough.

The detector 1 including the detecting element 10 and two second electrodes 11 is put in the holder 2, and is fixed by driving in the ring 3 into the holder 2 from above the detector 1.

A configuration where the detector 1 is mounted on the object gas pipe 22 is shown in FIG. 3. FIG. 3 is a view from direction A in FIG. 1A, and shows only the object gas pipe 22 cut off. Arrows in FIG. 3 shows a flowing direction of the object gas. The detector 1 is held with the holder 2 and ring 3 in parallel with flow of the object gas, and thus, a pressure of the object gas is applied almost equally to both sides of the detector 1. Therefore, contrary to the prior art, the electrolyte film 8 in the detector 1 is not exposed to a differential pressure of several atmospheres between the object gas and the atmosphere. Hence, the electrolyte film 8 is hardly broken. Even if an unexpected large stress breaks the electrolyte film 8, the object gas does not leak to the atmosphere. As a result, no safety valve is needed, which results in a very simple structure.

In FIG. 4, the detector 1 is connected to a direct-current power source 12 and an ampere meter 13 as current detecting structure through the output cable 7. The ampere meter 13 is connected to a microcomputer 14 as a concentration calculating section for determining concentration of carbon monoxide in the object gas from a detected current. The microcomputer 14 calculates a current difference (i.e., current change speed) at every specific time (for example, one second), and thus produces a resultant concentration of carbon monoxide while referring to a correlation table. The table, which is stored in an ROM, shows a correlation between current change speed and concentration of carbon monoxide.

An operation of the carbon monoxide sensor of the embodiment will be explained.

In this embodiment, oxygen gas cannot be introduced because the detector 1 in its entirety is disposed in the object gas. Therefore, cell reaction as in the prior art does not take place. In the embodiment, therefore, the sensor detects concentration of carbon monoxide according to the following operation.

Object gas containing much hydrogen, such as fuel gas supplied in a fuel cell, reaches the detector 1 and passes through the penetration holes 15 of the second electrodes 11, and reaches the detecting element 10. Since first electrodes 9 included in the detecting element 10 are mostly made of a carbon cloth, the object gas diffuses in the carbon cloth and reaches the carbon powder carrying the platinum catalyst. The two first electrodes 9 are connected to positive and negative terminals of the direct-current power source 12, respectively. At the first terminals 9, hydrogen in the object gas reacts as shown in the following formulas:

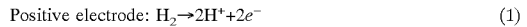
Positive electrode: $H_2 \rightarrow 2H^+ + 2e^-$ (1)

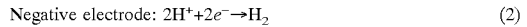
Negative electrode: $2H^+ + 2e^- \rightarrow H_2$ (2)

As shown in formula (1), hydrogen is dissociated at the first electrode 9 of a positive electrode side, and produced proton ($H^+$) passes through the electrolyte film 8 and reaches the first electrode 9 of a negative electrode side. As a result, as shown in formula (2), electron $e^-$ is received again, and hydrogen is produced. Therefore, the hydrogen forms a closed circuit between the detecting element 10 and direct-current power source 12, and a current depending on proton conductivity flows along the circuit.

If carbon monoxide is contained in the object gas, a surface of the platinum catalyst is poisoned as the carbon monoxide is adsorbed. This prevents the circuit from reacting as shown in formulas (1) and (2), and decreases a current. Therefore, monitoring this current provides an output corresponding to concentration of the carbon monoxide.

FIG. 5 shows an output current characteristic of the detecting element 10 through which object gas passes. In FIG. 5, the axis of abscissas denotes time, and the axis of ordinates represents output current. A voltage of about 0.4V is applied to the detecting element 10. When concentration of carbon monoxide is 0 ppm, the output current is constant. When carbon monoxide is mixed in the object gas, the output current decreases according to time. As shown in FIG. 5, a decreasing speed of the output current differs depending on concentration of carbon monoxide; that is, the higher the concentration, the faster the decreasing speed of the output current. This is so because the platinum catalyst is poisoned in a shorter time as concentration of carbon monoxide is higher. The microcomputer 14 determines this changing speed of output current by the changing amount of the output current at every specific time (for example, one second), and detects concentration of carbon monoxide. This means that the response time of this sensor is one second.

For comparison, a response time is measured in a conventional carbon monoxide sensor employing cell reaction between hydrogen and oxygen. Output potential changes in several minutes after 50 ppm of carbon monoxide flows. This shows that the carbon monoxide sensor according to the embodiment has a much shorter response time than does the conventional sensor.

Figure 13:
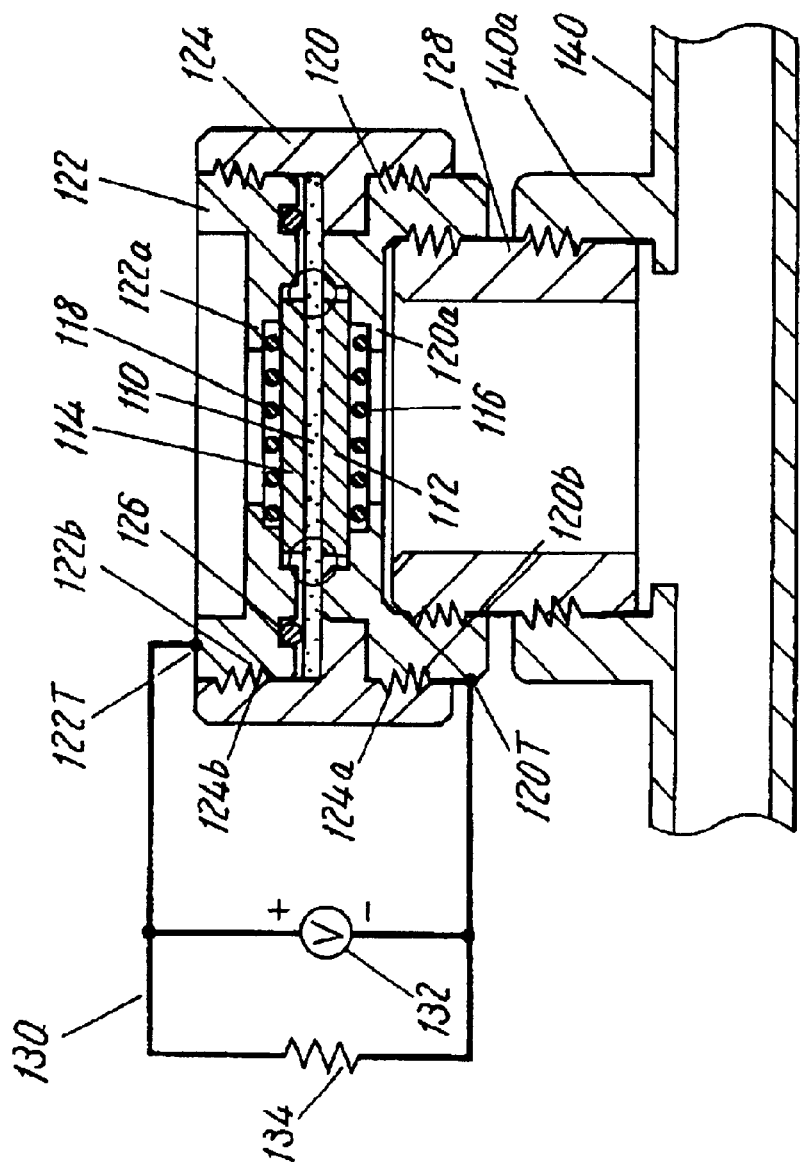
FIG. 13 is a schematic sectional view of a conventional carbon monoxide sensor.
Figure 14:
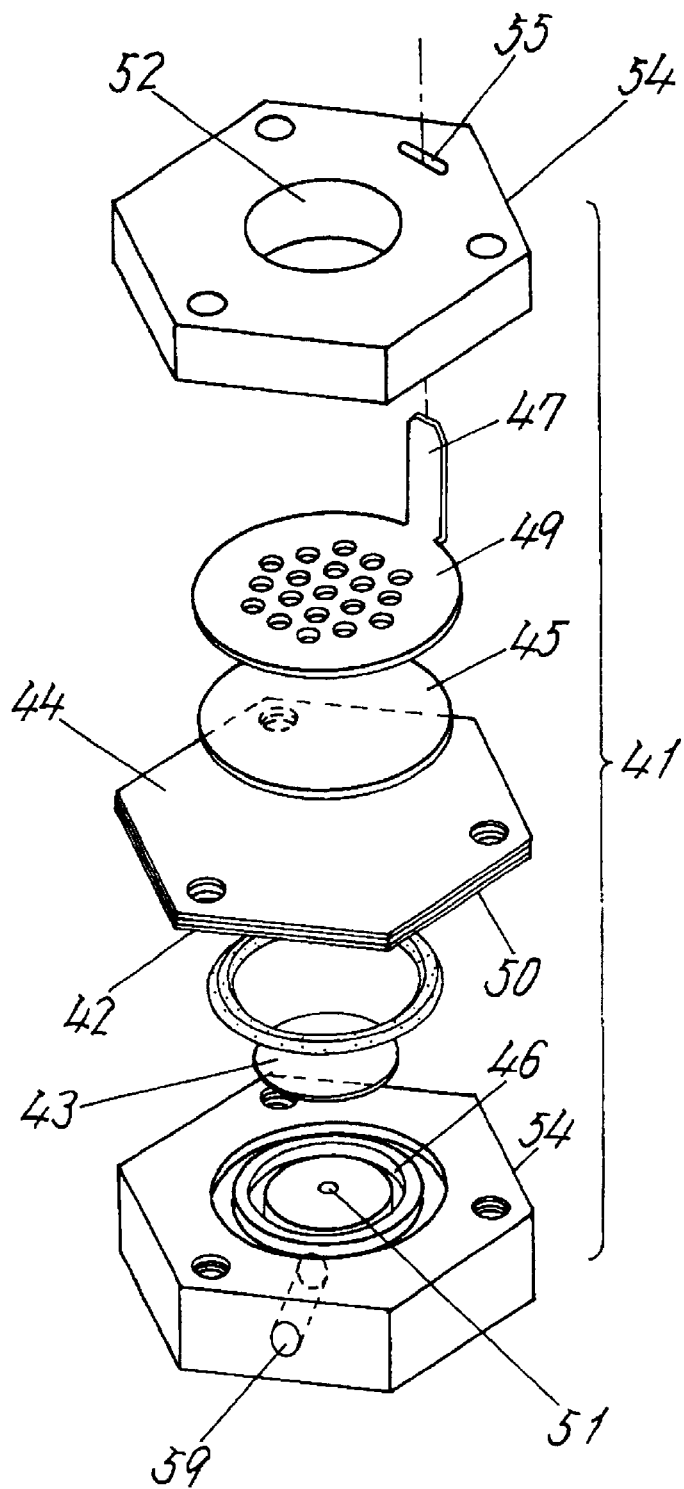
FIG. 14 is a perspective exploded view of a schematic structure of the conventional carbon monoxide sensor.

In a conventional sensor shown in FIG. 13, electrodes 112, 114 contacting with mesh metal plates 116, 118, with point contact or line contact, makes output voltage unstable and makes noise notable. In the sensor according to the embodiment, the second electrodes 11 having flat plates whose surfaces are smoothed and plated with gold contact widely with the first electrodes 9. Therefore, an extremely stable output current is obtained.

According to the embodiment, an ordinary ampere meter is used as a current detecting unit. But, the embodiment is not limited to this, and various current detecting devices, such as a current transformer, may be used.

According to the embodiment, applied voltage to the detecting element 10 is about 0.4V based on the following reason.

In order to determine voltage of the direct-current power source 12, a poisoning characteristic is measured while object gas containing carbon monoxide passes along with the various applied voltage. An applied voltage exceeding 1V makes an output current very unstable. This is so because the platinum catalyst in the first electrodes 9 is too highly activated with a high applied voltage, and carbon monoxide is adsorbed and simultaneously desorbed. The carbon monoxide adsorbed on the platinum catalyst (poisoning) prevents the catalyst from originally functioning and declines the output current. But soon after that, the carbon monoxide is desorbed, and the output current starts increasing again. This process, which is repeated randomly, makes the output current extremely unstable.

To obtain a stable output current, applied voltage should be lower than 1V. However, if the applied voltage is less than 0.1V, the voltage makes the output current too small to be distinguished from noise. Therefore, in order to obtain a favorable output current, an appropriate applied voltage ranges from 0.1V to 1V. However, as the applied voltage increases, the output current increases along with power consumption, and hence a shape and size of the electrodes must be designed appropriately.

From a comprehensive viewpoint of stability of the output current, sensitivity, noise, and shape and size of electrodes, the applied voltage preferably ranges from 0.3V to 0.8V, and more preferably from 0.4V to 0.5V.

Exemplary Embodiment 2

Figure 6:
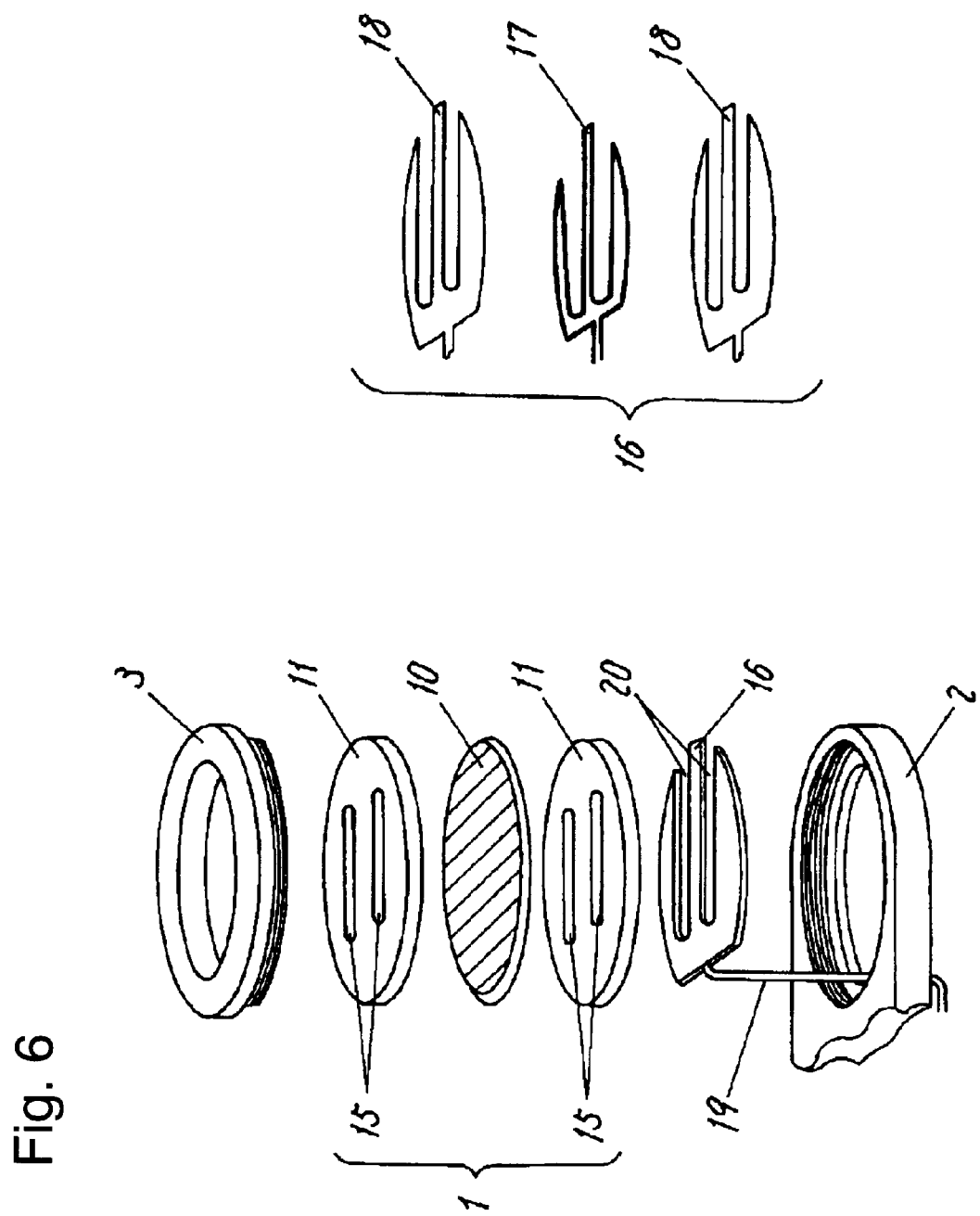
FIG. 6 is a perspective exploded view of a detector of a carbon monoxide sensor according to Exemplary Embodiment 2 of the invention.
Figure 7:
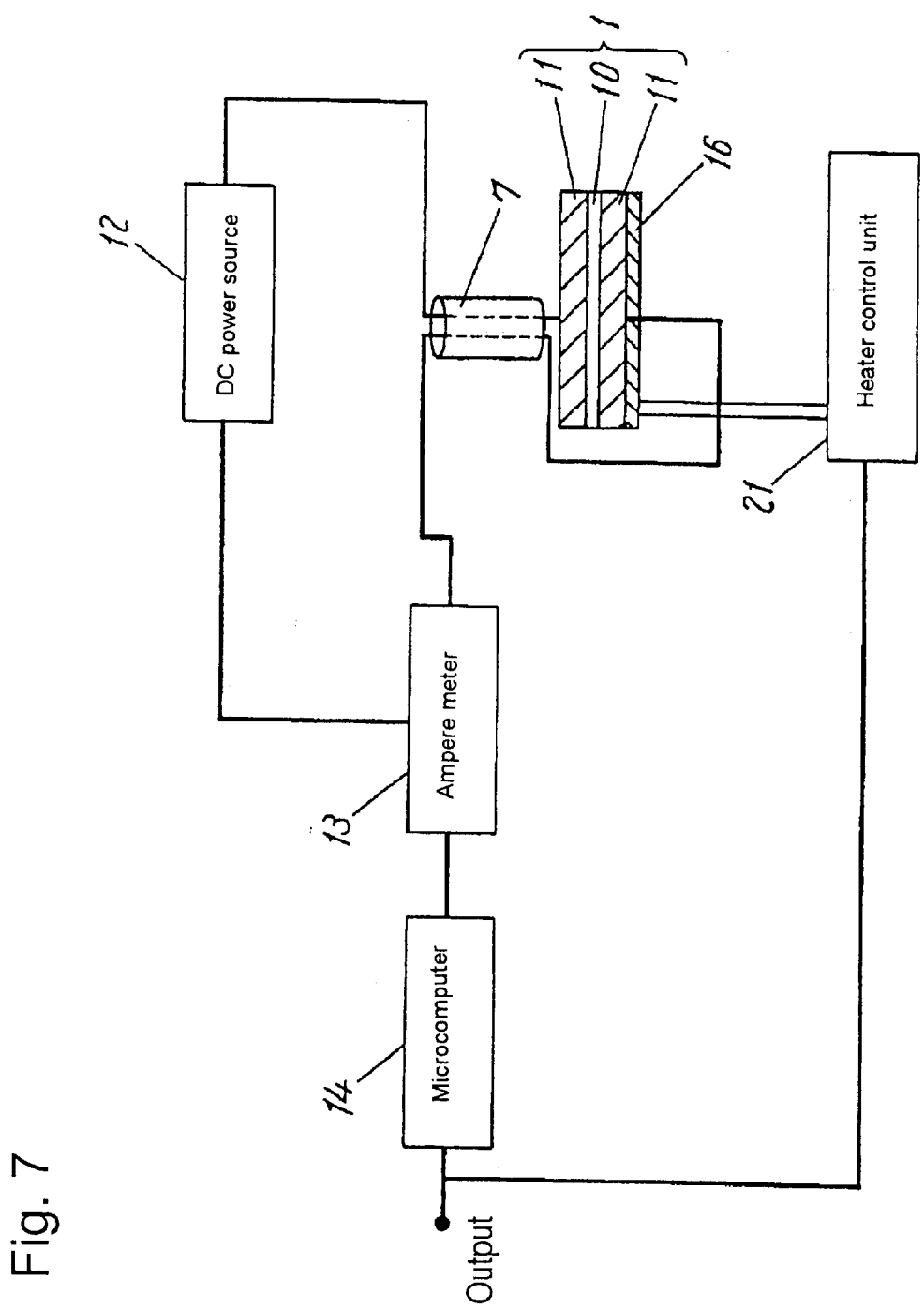
FIG. 7 is a block diagram of a detecting circuit of the carbon monoxide sensor according to Exemplary Embodiment 2 of the invention.

FIG. 6 is a perspective exploded view of a detector of a carbon monoxide sensor according to Exemplary Embodiment 2 of the invention. FIG. 7 is a block diagram of a detecting circuit.

In this embodiment, the same parts as in Exemplary Embodiment 1 are denoted by the same reference numerals, and detailed description thereof is omitted, and only differences between the embodiments will be explained.

The carbon monoxide sensor in Exemplary Embodiment 1 does not include a unit for desorbing carbon monoxide from the platinum catalyst by force after the platinum catalyst is poisoned. Although sufficiently functioning as an alarm or switch for indicating that concentration of carbon monoxide exceeds a certain level, this sensor does not sufficiently function as a carbon monoxide sensor having a reversible function since a reaction is irreversible. According to Exemplary Embodiment 2, as shown in FIG. 6, a heater 16 for heating a poisoned platinum catalyst due to adsorption of carbon monoxide, to recover a function of the platinum catalyst, is disposed at one side of detector 1. In the heater 16, a heating element 17 made of a nichrome wire formed in a specified shape as shown in FIG. 6, is held by a high polymer sheets 18 of polytetrafluoroethylene, such as TEFLON, or a fluorine compound blanked in the same shape as the heating element. Further, a heater cable 19 is connected to the heating element 17 to supply current, and the heater 16 is formed as a flat plate by performing a hot pressing operation. Object gas passes through slits 20 formed in the heater 16. So long as the object gas passes through, penetration holes may be provided instead of the slits 20. A shape and size of penetration holes or slits are not particularly specified.

The heater 16 is disposed between the detector 1 and holder 2 as shown in FIG. 6. The heater 16 and detector 1 are held and fixed by driving ring 3 into the holder 2 from above the detector. The detector 1 composed in this way is inserted and fixed in mounting threaded portion 4 in a manner similar to that associated with FIG. 1A and FIG. 1B.

The detecting circuit shown in FIG. 7 is composed by adding a heater control circuit 21 to the detecting circuit according to Exemplary Embodiment 1 shown in FIG. 4.

An operation of the carbon monoxide sensor according to Exemplary Embodiment 2 will be explained. A basic operation is the same as that of Exemplary Embodiment 1, except for operation of the heater 16 according to this embodiment. That is, by heating the platinum catalyst with the heater 16 to desorb carbon monoxide adsorbed in the platinum catalyst, the carbon monoxide sensor functions again.

When judging more concentration of carbon monoxide than a specified concentration, microcomputer 14 sends a judging signal to the heater control circuit 21. Then, the heater control circuit 21 supplies a current to the heater 16 for heating it to a temperature of about 130° C. As a result, the detector 1 is heated, and thus the carbon monoxide adsorbed in the platinum catalyst is desorbed. Therefore, even if the platinum catalyst is poisoned, the carbon monoxide sensor functions repeatedly.

Such carbon monoxide sensor has basically the same output current characteristic as that shown in FIG. 5. After the heater 16 operates to be heated to 130° C. after poisoning, the heater 16 is turned off to cool down, and the output current is measured again for an object gas containing 0 ppm concentration of carbon monoxide. As a result, the original output current is nearly recovered. Thus, a carbon monoxide sensor, capable of recovering a detecting function reversibly even after being poisoned, is obtained.

According to Exemplary Embodiments 1 and 2, the detector 1 is disposed substantially in parallel with flow of an object gas, but the detector may be disposed in any orientation so long as a pressure of the object gas can be applied almost equally to both sides of the detector 1.

Specific materials mentioned in Embodiments 1 and 2 are only examples for composing the carbon monoxide sensor of the invention, and are not limited only to these materials.

Thus, in spite of an extremely simple structure, a carbon monoxide sensor does not permit object gas to escape to the atmosphere.

Moreover, a carbon monoxide sensor is capable of recovering a detecting function even if poisoned.

Exemplary Embodiment 3

Figure 8:
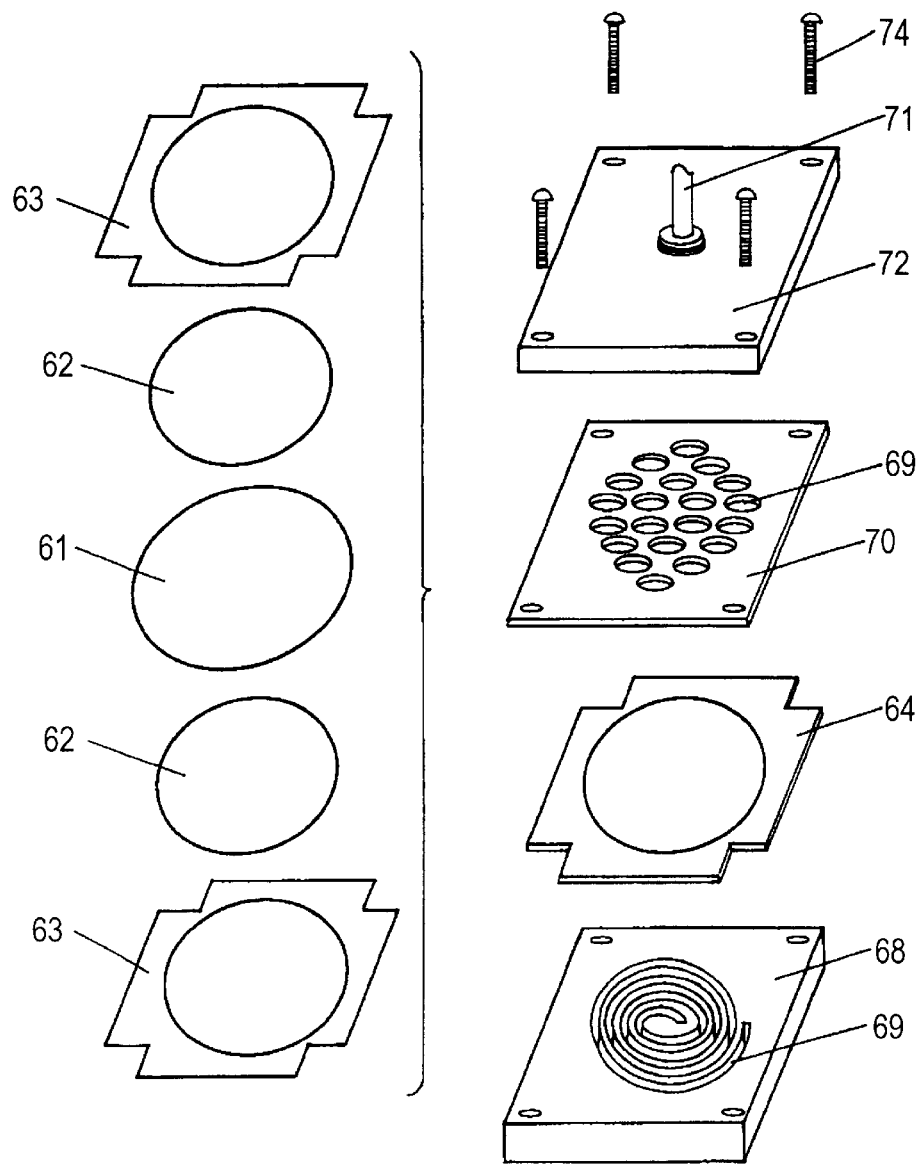
FIG. 8 is a perspective exploded view of a detector of a carbon monoxide sensor according to Exemplary Embodiment 3 of the invention.
Figure 9:
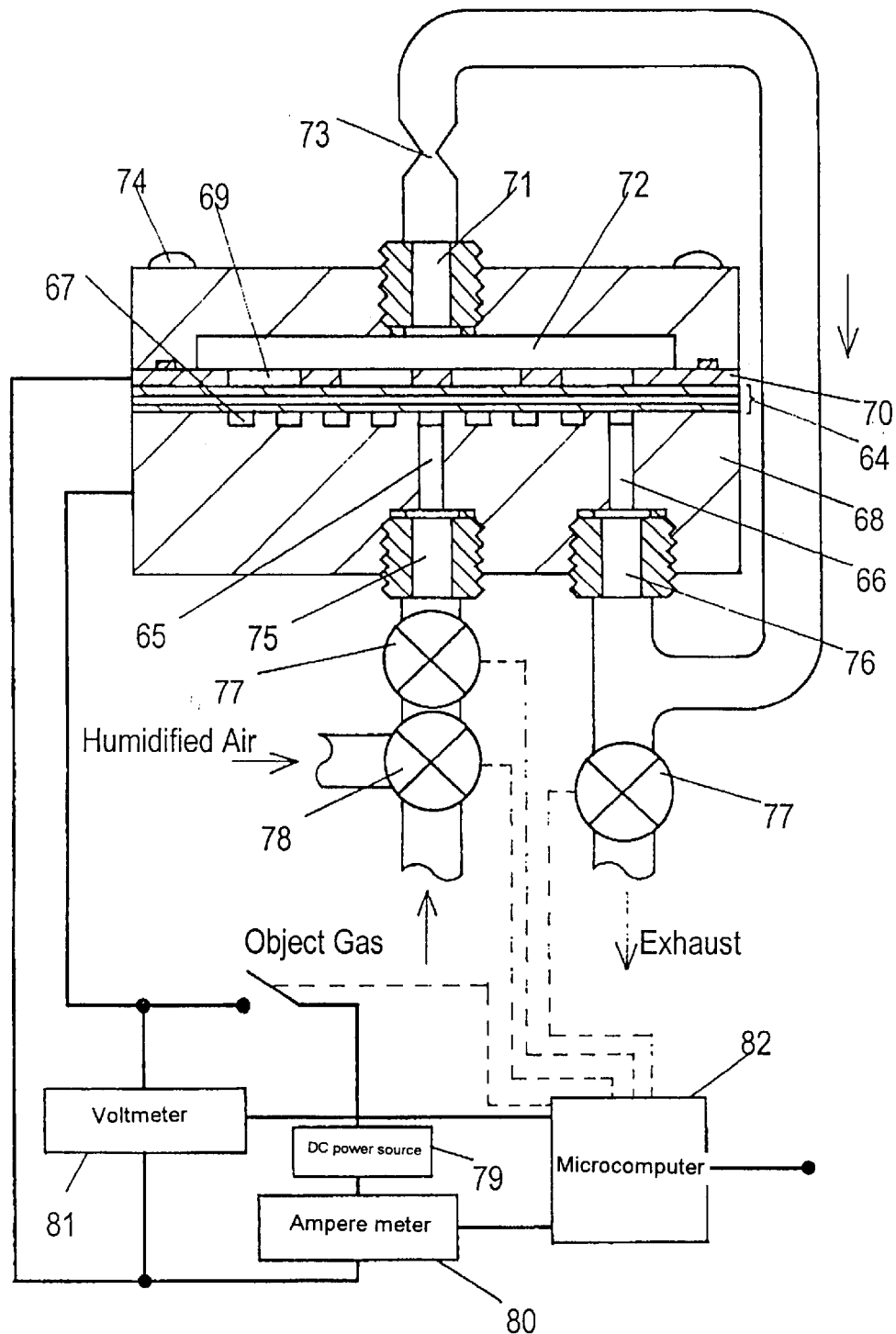
FIG. 9 is a block diagram of the carbon monoxide sensor according to Exemplary Embodiment 3 of the invention.
Figure 10:
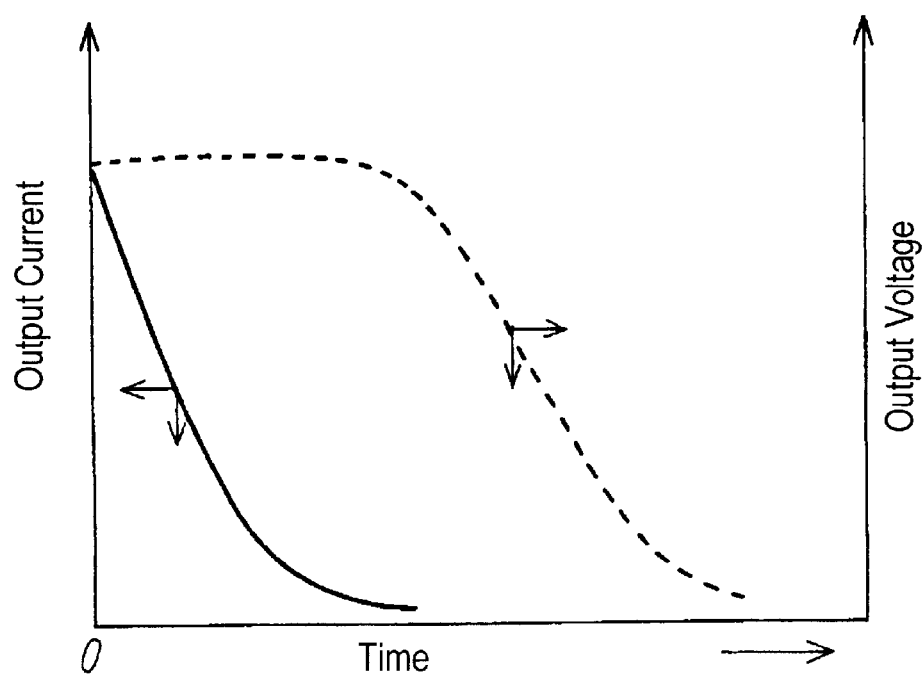
FIG. 10 is an output characteristic diagram of the carbon monoxide sensor according to Exemplary Embodiment 3 of the invention, and a prior art carbon monoxide sensor.

FIG. 8 is a perspective exploded view of a carbon monoxide sensor according to Exemplary Embodiment 3 of the present invention. FIG. 9 is a block diagram of the sensor. FIG. 10 is an output characteristic diagram of the sensor and a conventional sensor.

In FIG. 8, at both sides of a proton conductive electrolyte film 61 having a diameter of 1.4 cm and made of a fluorine high polymer material, upper and lower electrodes 62 are disposed. In each electrode, Provided is an alloy catalyst containing platinum and gold, at a ratio of 3:1 and carbon powder affixed on a carbon cloth having a diameter of 1 cm with a fluorine high polymer material. Outside of the two electrodes 62, seal members 63 made of a silicon high polymer having a thickness of 0.25 mm for preventing gas from leaking are provided. The proton conductive electrolyte film 61 held by the two electrodes 62 and seal members 63 is affixed by hot pressing at a temperature of 130° C. Thus, a detecting element 64 includes the proton conductive electrolyte film 61, two electrodes 62, and two seal members 63.

In FIG. 9, on one surface of the detecting element 64, a positive electrode current collector plate 68 contacts a gas passage 67 having a gas inlet 65 and a gas outlet 66. The gas passage 67 is formed, by cutting, a surface of the positive electrode current collector plate 68 made of stainless steel (for example, SUS304 of the JIS standard) in width and pitch of 0.5 mm and depth of 0.3 mm within an area of one of the electrodes 62. Dimensions of the gas passage 67 are not particularly specified so long as a specified gas flow rate is assured (50 cc/min. in Exemplary Embodiment 3). The surface of the positive electrode current collector plate 68 that is cut is plated with a gold layer of a thickness of 1 μm.

On another surface of the detecting element 64, a negative electrode current collector plate 70 made of stainless steel (for example, SUS304 of the JIS standard), in which multiple holes 69 having a diameter of 1.5 mm are formed, is disposed. A surface of the negative electrode current collector plate 70 is also plated with a gold layer having a thickness of 1 μm.

At a side of the negative electrode current collector plate 70 not contacting the detecting element 64, i.e., above the negative electrode current collector plate 70 in FIG. 9, a gas chamber 72, formed, by cutting stainless steel (for example, SUS304 of the JIS standard) and having a gas outlet 71, is disposed. An orifice 73 having a diameter of 0.8 mm is connected to the gas outlet 71 as a flow rate suppressing unit.

The positive electrode current collector plate 68, detecting element 64, negative electrode current collector plate 70, and gas chamber 72 are fixed in this order with four screws 74.

At the gas inlet 65 and outlet 66, a gas feed unit 75 and a gas exhausting unit 76, made of pipes having tapered threads are connected, respectively. At a leading end of the gas feed unit 75, provided is a valve 77 and a switching valve 78 for switching object gas with humidified air. Humidified air to be supplied into a fuel cell is partly branched and fed into the switching valve 78. Outlet sides of the gas exhausting unit 76 and orifice 73 are piped so as to be confluent, and the valve 77 is provided at the leading end.

The positive electrode current collector plate 68 and negative electrode current collector plate 70 are connected to positive and negative terminals of a direct-current power source 79, respectively. In order to detect current flowing between the positive electrode current collector plate 68 and negative electrode current collector plate 70, an ampere meter 80 is connected as a current detecting unit in series with the direct-current power source 79. In order to detect voltage between the positive electrode current collector plate 68 and negative electrode current collector plate 70, similarly, a voltmeter 81 is connected as a voltage detecting unit. Outputs of the ampere meter 80 and voltmeter 81 are connected to a microcomputer 82. The microcomputer 82 calculates a change speed of current, for example, at every one second from a current detected by the ampere meter 80, and thus produces a resultant concentration of carbon monoxide while referring to a correlation table. The table, which is stored in an ROM, shows a correlation between current and concentration of carbon monoxide. Further, the microcomputer 82 controls to turn on and off the direct-current power source 79, to operate the switching valve 78, and to open and close the valve 77 in order to recover (or refresh) a function of the catalyst adsorbing carbon monoxide.

An operation of the carbon monoxide sensor according to Exemplary Embodiment 3 will be explained below.

In order to suppress output fluctuations due to a drying of the proton conductive electrolyte film 61, the microcomputer 82 opens two valves 77 and switches the switching valve 78 to humidified air side to pass humidified air for thirty seconds. A flow rate of the humidified air is, for example, 50 cc/min. A duration of thirty seconds is necessary for replacing gas in sensor piping and gas passage 67 with humidified air at a flow rate of 50 cc/min. Therefore, since replacement time differs with flow rate and size of the gas passage 67, duration in Exemplary Embodiment 3 is not particularly specified.

Then, the microcomputer 82 switches the switching valve 78 to an object gas side. A flow rate of object gas is 50 cc/min. The object gas is led into the gas passage 67 through the valves 77, gas feed unit 75, and gas inlet 65. Since the gas passage 67 contacts one of the electrodes 62, the object gas diffuses uniformly into the carbon cloth composing this electrodes as the gas flows in the gas passage 67, and reaches the catalyst composed of an alloy of platinum and gold. The object gas is then exhausted through the outlet 66, gas exhausting unit 76, and valve 77.

After thirty seconds of the above operation, after the gas in the piping and gas passage 67 is replaced with an object gas, the microcomputer 82 turns on the direct-current power source 79. A voltage is applied between the positive electrode current collector plate 68 and negative electrode current collector plate 70. According to Exemplary Embodiment 3, the voltage is 0.1V. By this operation, hydrogen in the object gas reacts with the catalyst of the electrodes 62 as in the following formulas at the positive electrode and negative electrode, respectively:

Positive electrode: $H_2 \rightarrow 2H^+ + 2e^-$ (3)

Negative electrode: $2H^+ + 2e^- \rightarrow H_2$ (4)

At positive electrode 62, as shown in formula (3), the hydrogen is dissociated, and produced proton ($H^+$) reaches the negative electrode 62 through the proton conductive electrolyte film 61. Then, as shown in formula (4), electron ($e^-$) is received, and hydrogen is generated again. Therefore, the hydrogen forms an electrically closed circuit between the detecting element 64 and direct-current power source 79, and a current depending on the proton conductivity flows.

If carbon monoxide is contained in the object gas, a surface of the catalyst composed of an alloy of platinum and gold is poisoned as the carbon monoxide is adsorbed thereby. As a result, the reactions as shown in formulas (3) and (4) are prevented, current is decreased. The microcomputer 82 calculates a decreasing speed of the current at every second and produces a resultant concentration of carbon monoxide as an output by referring to a correlation table showing a correlation between current decreasing speed and concentration of carbon monoxide.

As this operation continues, the catalyst is poisoned by carbon monoxide, and the current flow decreases. The current changing speed at this time is much lower than that at the start of using the sensor at the same concentration of carbon monoxide, and thus a large detection error of concentration occurs. The microcomputer 82 measures the current decrease in the catalyst due to poisoning with carbon monoxide for a specific time (one minute in Exemplary Embodiment 3), and refreshes as follows.

First, the microcomputer 82 turns off the direct-current power source 79, and switches the switching valve 78 to a humidified air side. As a result, humidified air flows into the gas passage 67.

Hydrogen is being generated in the gas chamber 72 according to the reaction shown in formulas (3) and (4) until the switching valve 78 is switched. Further, the orifice 73 connected to the outlet 71 of the gas chamber 72 does not exhaust generated hydrogen immediately, and a specific volume of hydrogen remains in the gas chamber 72.

Therefore, the detecting element 64 forms a fuel cell composed of air in the gas passage 67 and hydrogen in the gas chamber 72, and generates an electromotive force. This electromotive force is generated with the positive electrode current collector plate 68 as a positive electrode and the negative electrode current collector plate 70 as a negative electrode. Voltage of the electromotive force increases to a peak of about 0.8V and then decreases gradually in Exemplary Embodiment 3. This is so because the hydrogen gas in the gas chamber 72 is gradually consumed for generating the electromotive force.

During the above operation, oxygen in the humidified air is supplied onto the poisoned catalyst, and reacts with carbon monoxide to form carbon dioxide and to be separated from the catalyst. Simultaneously, electrode 62 at the poisoned catalyst side generates an electromotive force of about 0.8V, which is more than 0.68V necessary for desorbing carbon monoxide adsorb by the catalyst, and thus carbon monoxide is separated from the catalyst. Therefore, humidified air fed into the gas passage 67 causes oxidation and an electromotive force to react on the poisoned catalyst, and refreshes the catalyst almost to its original state.

Voltage changes due to the electromotive force are monitored by the voltmeter 81 connected between the positive electrode current collector plate 68 and negative electrode current collector plate 70. The microcomputer 82 determines a voltage changing speed from output of the voltmeter 81 and judges that refreshing is over when the changing speed turns negative (that is, voltage decreases), and switches the switching valve 78 to the object gas side.

Consequently, the microcomputer 82 waits until humidified air in the piping and gas passage 67 is replaced by object gas (thirty seconds in Exemplary Embodiment 3), turns on the direct-current power source 79, and continues measuring a concentration of carbon monoxide.

By repeating this operation, concentration of the carbon monoxide is detected.

When stopping operation of the carbon monoxide sensor, the microcomputer 82 switches the switching valve 78 to the humidified air side, and refreshes the catalyst as mentioned above. When the voltage changing speed determined from an output of the voltmeter 81 turns negative, the microcomputer 82 closes two valves 77, and turns off the direct-current power source 79. As a result, the carbon monoxide sensor stops, and the detecting element 64 is always exposed to humidified air, so that output fluctuations due to drying of the proton conductive electrolyte film 61 can be suppressed.

In FIG. 10, the solid line shows an output characteristic when an object gas containing 20 ppm of carbon monoxide flows in the carbon monoxide sensor according to Exemplary Embodiment 3 at flow rate of 50 cc/min. The axis of abscissas shows time, and the axis of ordinates indicates an output current. At time of 0, direct-current power source 79 is turned on. Simultaneously with turning-on of the direct-current power source 79, an output current begins to decrease. By calculating this changing speed, microcomputer 82 detects a concentration of carbon monoxide. In FIG. 10, the broken line denotes a characteristics of the prior art, in which output voltage does not change for several minutes for the same object gas.

In this sensor, an object gas diffuses quickly into electrodes 62 having the catalyst through the gas passage 67, and causes poisoning during an early stage. A slow reaction of forming water from proton, electron and oxygen does not substantially take place. Further, the catalyst made of an alloy of platinum and gold is poisoned extremely quickly by carbon monoxide. Hence, as compared with the prior art, the carbon monoxide sensor of Exemplary Embodiment 3 reacts extremely fast.

In Exemplary Embodiment 3, as the catalyst composing electrodes 62, an alloy of platinum and gold, which is likely to be poisoned by carbon monoxide, is used. However, with regard to the catalyst used in the negative electrode current collector plate 70 functioning as the negative electrode it is not necessary to consider the poisoning by carbon monoxide. Consequently, the negative electrode current collector plate 70 may be made of platinum only, or an alloy of platinum and another noble metal, for example, platinum and ruthenium, and thus an alloy material of platinum and gold is not particularly specified.

Exemplary Embodiment 4

Figure 11:
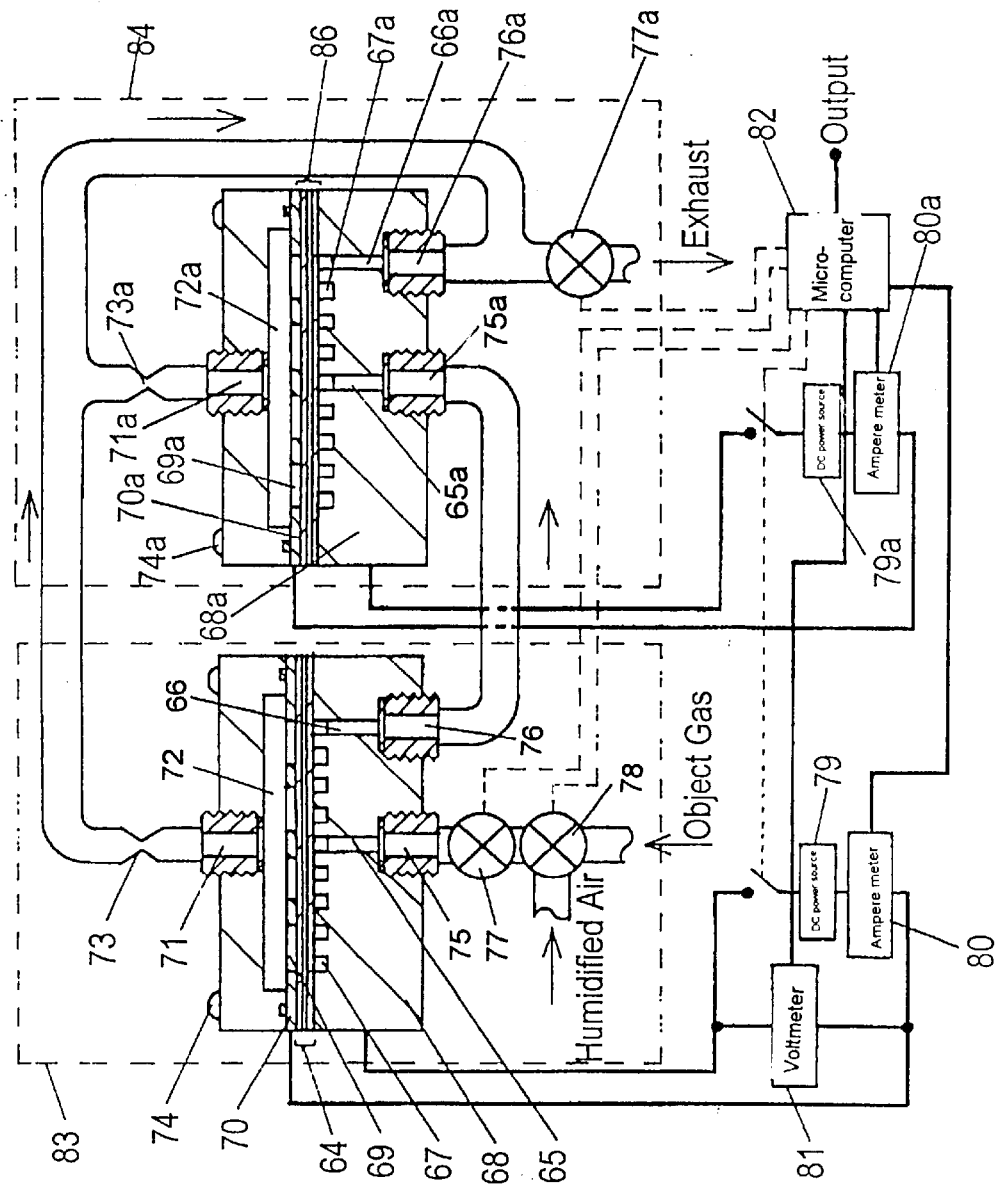
FIG. 11 is a block diagram of a carbon monoxide sensor according to Exemplary Embodiment 4 of the invention.
Figure 12:
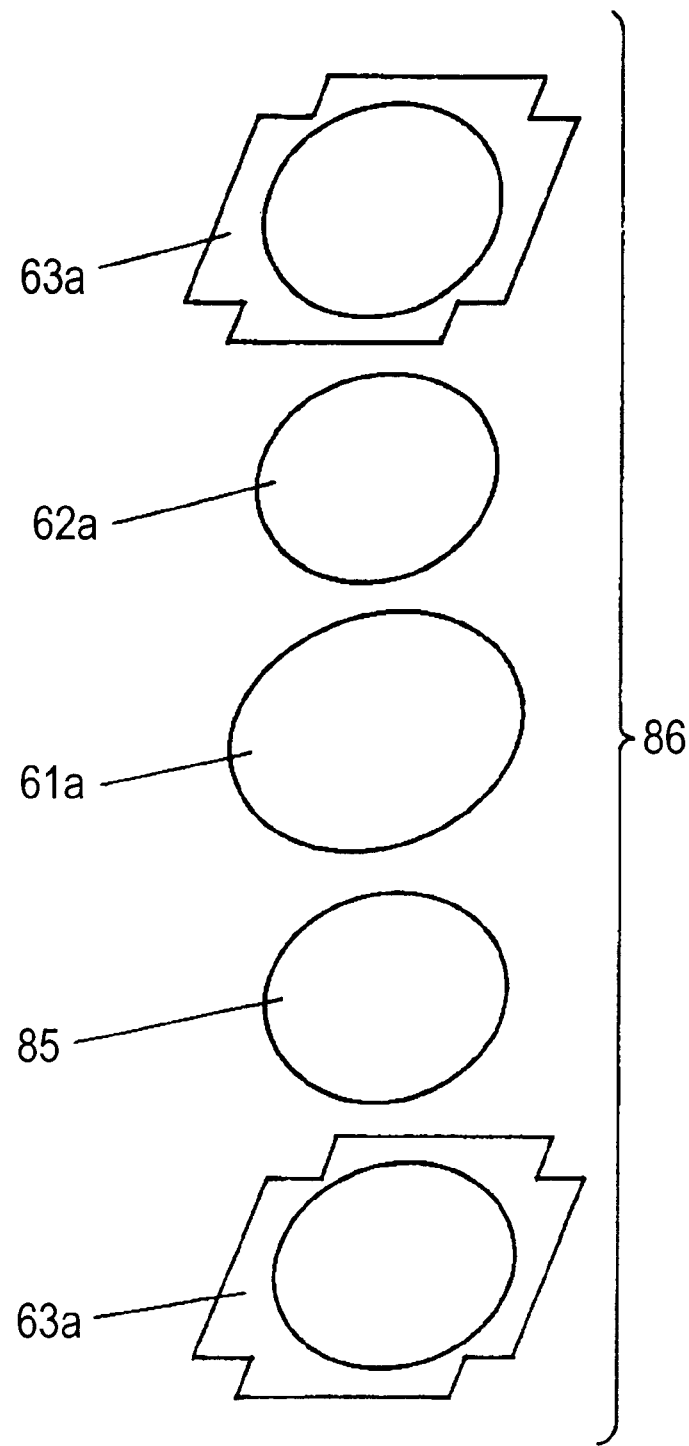
FIG. 12 is a perspective exploded view of a detecting element of the carbon monoxide sensor according to Exemplary Embodiment 4 of the invention.

FIG. 11 is a block diagram of a carbon monoxide sensor according to Exemplary Embodiment 4 of the present invention. FIG. 12 is a perspective exploded view of a second detecting element of the carbon monoxide sensor according to Exemplary Embodiment 4 of the invention.

In Exemplary Embodiment 4, the carbon monoxide sensor, which is generally the same as that in Exemplary Embodiment 3 (hereinafter carbon monoxide detector 83), is combined with a hydrogen detector 84. A catalyst of a positive electrode of hydrogen detector 84 is made of an alloy of platinum and ruthenium. A circuit of the hydrogen detector 84 is the same as that in the carbon monoxide detector 83 except that voltmeter 81 is not connected.

The same parts as in Exemplary Embodiment 3 are denoted by the same reference numerals, and a detailed description thereof is omitted. Names of the parts used in the carbon monoxide detector 83 are preceded by a word "first", and those of the parts used in the hydrogen detector 84 are distinguished by a preceding word "second" and subscript "a" attached to the reference numerals.

In FIG. 12, a catalyst electrode 85 includes carbon powder carrying a catalyst made of an alloy of platinum and ruthenium, which is affixed on a carbon cloth having a diameter of 1 cm, with a fluorine high polymer material. Other parts including proton conductive electrolyte film 61, electrode 62, and seal member 63 are the same as those explained with regard to FIG. 8.

During a measurement with the carbon monoxide sensor explained with regard to Exemplary Embodiment 3, if a concentration of hydrogen in an object gas changes largely, an amount of protons flowing in the proton conductive electrolyte film 61 varies, and an output current also changes. It may therefore be hard to determine whether the output current changes according to a change of a concentration of carbon monoxide or hydrogen. Consequently, the carbon monoxide sensor explained with regard to Exemplary Embodiment 3 operates sufficiently to detect a concentration of carbon monoxide under a limited condition, i.e., so long as operation of a reformer is stable, and concentration of hydrogen from the reformer is almost constant. However, the sensor may not exhibit sufficient performance, for example, right after the reformer starts operating or when concentration of hydrogen fluctuates.

According to Exemplary Embodiment 4, as shown in FIG. 11, the hydrogen detector 84 for detecting only a concentration of hydrogen is connected to a first gas exhausting unit 76 of the carbon monoxide detector 83. Concentration of carbon monoxide is compensated according to a change of concentration of hydrogen, and issued.

A basic operation of the carbon monoxide sensor according to Exemplary Embodiment 4 will be explained. Microcomputer 82 opens two valves 77, 77a, switches switching valve 78 to a humidified air side, and waits for sixty seconds. A flow rate of humidified air is set to 50 cc/min.

Then, the microcomputer 82 switches the switching valve 78 to object gas side. A flow rate of object gas is set to 50 cc/min. The object gas flows through the first valve 77, first gas feed unit 75 and first inlet 65 of the carbon monoxide detector 83, and is guided into the first gas passage 67 to contact a catalyst made of an alloy of platinum and gold in electrode 62. Then, the object gas passes through first outlet 66 and first gas exhausting unit 76. The gas further passes through second gas feed unit 75a and second inlet 65a of the hydrogen detector 84, and is guided into the second gas passage 67a to reach catalyst electrode 85, made of an alloy of platinum and ruthenium, in second detecting element 86. The object gas is exhausted through second outlet 66a, second gas exhausting unit 76a, and second valve 77a.

Sixty seconds after the switching valve 78 is switched to the object gas side, the gas in piping, and the first gas passage 67 and second gas passage 67a, is replaced by object gas. Then, the microcomputer 82 turns on first direct-current power source 79 and second direct-current power source 79a of the carbon monoxide detector 83 and hydrogen detector 84 at the same time. These power sources apply voltages between first positive electrode current collector plate 68 and first negative electrode current collector plate 70, and between second positive electrode current collector plate 68a and second negative electrode current collector plate 70a. In Exemplary Embodiment 4, a voltage of each detector is set to 0.1V. In each detector, hydrogen in the object gas reacts at the catalysts of electrodes 62 and catalyst electrode 85 in the positive and negative electrodes as shown in the following formulas, and a current depending on proton conductivity flows in each detector.

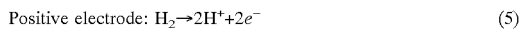

Positive electrode: $H_2 \rightarrow 2H^+ + 2e^-$ (5)

Negative electrode: $2H^+ + 2 \rightarrow H_2$ (6)

Under this condition, carbon monoxide in the object gas is adsorbed in a surface of the catalyst made of an alloy of platinum and gold in the first detecting element 64 of the carbon monoxide detector 83, and poisons the catalyst. Then, the absorbed carbon monoxide prevents the carbon monoxide detector 83 from reacting as shown in formulas (5) and (6), and decreases a current. Because of the carbon monoxide adsorbed in the catalyst of the carbon monoxide detector 83, an object gas almost containing no carbon monoxide flows into the hydrogen detector 84. The second detecting element 86, having the catalyst electrode 85 made of an alloy of platinum and ruthenium which is hardly poisoned by carbon monoxide, outputs current depending on concentration of hydrogen without an affect of carbon monoxide.

The microcomputer 82 calculates a decreasing speed of the current of the carbon monoxide detector 83 at every second, and issues a concentration of carbon monoxide by referring to a correlation table of concentration of carbon monoxide determined from a current changing speed and an output current of the hydrogen detector 84.

After the sensor continues to output a concentration of carbon monoxide for a specific time (sixty seconds in Exemplary Embodiment 4), the microcomputer 82 refreshes the sensor in the same manner as in Exemplary Embodiment 3.

Upon waiting for the object gas to replace humidified air in the piping and the first gas passage 67 and second gas passage 67a (sixty seconds in Exemplary Embodiment 4), the microcomputer 82 turns on the first direct-current power source 79 and second direct-current power source 79a at the same time, and continues to measure a concentration of carbon monoxide for a specific time (sixty seconds in Exemplary Embodiment 4).

By repeating the above operation, the sensor detects a concentration of carbon monoxide.

When stopping operation of the carbon monoxide sensor, in a manner similarly to that for Exemplary Embodiment 3, the microcomputer 82 switches the switching valve 78 to the humidified air side, and refreshes the sensor as mentioned above. When a voltage changing speed determined from an output of the voltmeter 81 turns negative, the microcomputer 82 closes two valves 77, 77a, and turns off the first direct-current power source 79 and second direct-current power source 79a, and then, stops the carbon monoxide sensor. The first detecting element 64 and second detecting element 86 are always exposed to humidified air, so that output fluctuations due to a drying of the first proton conductive electrolyte film 61 and second proton conductive electrolyte film 61a can be suppressed.

In the carbon monoxide sensor according to Exemplary Embodiment 4, from a measurement of an output for an object gas containing 20 ppm of carbon monoxide flowing at flow rate of 50 cc/min, it has been confirmed that obtained is the same high response performance as was obtained with regard to Exemplary Embodiment 3. This is so because of the following reasons:

(i) The object gas diffuses quickly in the first electrodes 62, having the catalyst, through the first gas passage 67, thereby causing poisoning during an early stage;

(ii) A chemical reaction having a slow rate like forming water from protons, electrons and oxygen does not substantially occur; and (iii) A catalyst made of an alloy of platinum and gold is poisoned extremely quickly by carbon monoxide.

Moreover, even if concentration of hydrogen in the object gas is varied, the sensor accurately detects a concentration of carbon monoxide.

Material used in Exemplary Embodiments 3 and 4 is just an example for providing the carbon monoxide sensor of the invention, and is not particularly specified.

Thus, a carbon monoxide sensor having an extremely fast response is obtained. Even if hydrogen concentration in the object gas varies, the carbon monoxide sensor is capable of accurately detecting a carbon monoxide concentration.

INDUSTRIAL APPLICABILITY

The invention presents a carbon monoxide sensor that does not allow an object gas to leak into the atmosphere in spite of a very simple structure of the sensor.

The invention presents a carbon monoxide sensor having an excellent response performance, that is capable of detecting concentration utilizing a proton conductivity without inducing chemical reaction of a slow rate for generating water and electricity from protons, electrons and oxygen.

What is claimed is:

1. A carbon monoxide sensor comprising:
   a detector to be disposed in an object gas containing hydrogen, said detector including
   (i) a proton conductive electrolyte film having first and second sides,
   (ii) a first electrode on said first side of said proton conductive electrolyte film,
   (iii) a second electrode on said first electrode,
   (iv) a third electrode on said second side of said proton conductive electrolyte film, and
   (v) a fourth electrode on said third electrode;
   a power source having positive and negative terminals coupled to said first and third electrodes, respectively; and a current detecting device for detecting a current that changes in response to concentration of carbon monoxide in the object gas.

2. The carbon monoxide sensor according to claim 1, wherein
said first electrode includes
(a) a carbon cloth, and
(b) carbon powder, carrying a catalyst, affixed to said carbon cloth,
said second electrode has a penetration hole therein,
said third electrode includes
(a) a carbon cloth, and
(b) carbon powder, carrying a catalyst, affixed to said carbon cloth, and
said fourth electrode has a penetration hole therein.

3. The carbon monoxide sensor according to claim 2, wherein
a surface of said second electrode is smoothly pressed and plated with a gold layer, and
a surface of said fourth electrode is smoothly pressed and plated with a gold layer.

4. The carbon monoxide sensor according to claim 2, further comprising:
a concentration calculating device for calculating concentration of carbon monoxide from the current detected by said current detecting device.

5. The carbon monoxide sensor according to claim 4, wherein
said concentration calculating device includes a calculating unit for converting a changing speed of the current detected by said current detecting device to concentration of carbon monoxide.

6. The carbon monoxide sensor according to claim 2, further comprising:
a heater in said detector; and
a heater control unit for controlling said heater.

7. The carbon monoxide sensor according to claim 6, wherein
said heater includes
(i) a heating element, and
(ii) a sheet for holding said heating element,
with said heating element and said sheet each have one of a hole and a slit penetrating therethrough.

8. The carbon monoxide sensor according to claim 7, wherein
said sheet comprises a fluorine high polymer sheet.

9. The carbon monoxide sensor according to claim 2, wherein
said detector is to be disposed in an object gas by being disposed parallel to a flow of the object gas.

10. The carbon monoxide sensor according to claim 2, wherein
said power source is designed such that a voltage thereof ranges from 0.1V to 1.0V.

11. A carbon monoxide sensor comprising:
a detector to be disposed in an object gas containing hydrogen, said detector including
(i) a proton conductive electrolyte film having first and second sides,
(ii) a first electrode on said first side of said proton conductive electrolyte film, and
(iii) a second electrode on said second side of said proton conductive electrolyte film;
a power source having positive and negative terminals coupled to said first and second electrodes, respectively;
a current detecting device for detecting a current that changes in response to concentration of carbon monoxide in the object gas; and
a concentration calculating device for calculating concentration of carbon monoxide from a changing speed of the current detected by said current detecting device.

12. The carbon monoxide sensor according to claim 11, wherein
said first electrode includes
(i) a carbon cloth, and
(ii) carbon powder, carrying a catalyst, affixed to said carbon cloth,
said second electrode includes
(i) a carbon cloth, and
(ii) carbon powder, carrying a catalyst, affixed to said carbon cloth, and
said detector further comprises a third electrode on said first electrode, and a fourth electrode on said second electrode, with each of said third electrode and fourth electrode having a penetration hole therein.

13. The carbon monoxide sensor according to claim 12, wherein
a surface of said third electrode is smoothly pressed and plated with a gold layer, and
a surface of said fourth electrode is smoothly pressed and plated with a gold layer.

14. The carbon monoxide sensor according to claim 11, further comprising:
a heater in said detector; and
a heater control unit for controlling said heater.

15. The carbon monoxide sensor according to claim 14, wherein
said heater includes
(i) a heating element, and
(ii) a sheet for holding said heating element,
with said heating element and said sheet each have one of a hole and a slit penetrating therethrough.

16. The carbon monoxide sensor according to claim 15, wherein
said sheet comprises a fluorine high polymer sheet.

17. The carbon monoxide sensor according to claim 11, wherein
said detector is to be disposed in an object gas by being disposed parallel to a flow of the object gas.

18. The carbon monoxide sensor according to claim 11, wherein
said power source is designed such that a voltage thereof ranges from 0.1V to 1.0V.

19. A carbon monoxide sensor comprising:
a detector to be disposed in an object gas containing hydrogen, said detector including
(i) a proton conductive electrolyte film having first and second sides,
(ii) a first electrode on said first side of said proton conductive electrolyte film, and
(iii) a second electrode on said second side of said proton conductive electrolyte film;
a power source having positive and negative terminals coupled to said first and second electrodes, respectively;
a current detecting device for detecting a current that changes in response to concentration of carbon monoxide in the object gas;
a heater in said detector, said heater including (i) a heating element, and
(ii) a fluorine high polymer sheet for holding said heating element,
with said heating element and said fluorine high polymer sheet each having one of a hole and a slit penetrating therethrough; and
a heater control unit for controlling said heater.

20. The carbon monoxide sensor according to claim 19, wherein
said first electrode includes
(i) a carbon cloth, and
(ii) carbon powder, carrying a catalyst, affixed to said carbon cloth,
said second electrode includes
(i) a carbon cloth, and
(ii) carbon powder, carrying a catalyst, affixed to said carbon cloth, and
said detector further comprises a third electrode on said first electrode, and a fourth electrode on said second electrode, with each of said third electrode and fourth electrode having a penetration hole therein.

21. The carbon monoxide sensor according to claim 20 wherein
a surface of said third electrode is smoothly pressed and plated with a gold layer, and
a surface of said fourth electrode is smoothly pressed and plated with a gold layer.

22. The carbon monoxide sensor according to claim 19, further comprising:
a concentration calculating device for calculating concentration of carbon monoxide from the current detected by said current detecting device.

23. The carbon monoxide sensor according to claim 22, wherein
said concentration calculating device includes a calculating unit for converting a changing speed of the current detected by said current detecting device to concentration of carbon monoxide.

24. The carbon monoxide sensor according to claim 19, wherein
said detector is to be disposed in an object gas by being disposed parallel to a flow of the object gas.

25. The carbon monoxide sensor according to claim 19, wherein
said power source is designed such that a voltage thereof ranges from 0.1V to 1.0V.

26. A carbon monoxide sensor comprising:
a detector to be disposed in an object gas containing hydrogen, said detector including
(i) a proton conductive electrolyte film having first and second sides,
(ii) a first electrode on said first side of said proton conductive electrolyte film, and
(iii) a second electrode on said second side of said proton conductive electrolyte film;
a power source having positive and negative terminals coupled to said first and second electrodes, respectively;
a current detecting device for detecting a current that changes in response to concentration of carbon monoxide in the object gas;
a heater in said detector; and
a heater control unit for energizing said heater when concentration of carbon monoxide in the object gas exceeds a predetermined value.

27. The carbon monoxide sensor according to claim 26, wherein
said first electrode includes
(i) a carbon cloth, and
(ii) carbon powder, carrying a catalyst, affixed to said carbon cloth,
said second electrode includes
(i) a carbon cloth, and
(ii) carbon powder, carrying a catalyst, affixed to said carbon cloth, and said detector further comprises a third electrode on said first electrode, and a fourth electrode on said second electrode, with each of said third electrode and fourth electrode having a penetration hole therein.

28. The carbon monoxide sensor according to claim 27, wherein
a surface of said third electrode is smoothly pressed and plated with a gold layer, and
a surface of said fourth electrode is smoothly pressed and plated with a gold layer.

29. The carbon monoxide sensor according to claim 26, further comprising:
a concentration calculating device for calculating concentration of carbon monoxide from the current detected by said current detecting device.

30. The carbon monoxide sensor according to claim 29, wherein
said concentration calculating device includes a calculating unit for converting a changing speed of the current detected by said current detecting device to concentration of carbon monoxide.

31. The carbon monoxide sensor according to claim 26, wherein
said heater includes
(i) a heating element, and
(ii) a sheet for holding said heating element,
with said heating element and said sheet each have one of a hole and a slit penetrating therethrough.

32. The carbon monoxide sensor according to claim 31, wherein
said sheet comprises a fluorine high polymer sheet.

33. The carbon monoxide sensor according to claim 26, wherein
said detector is to be disposed in an object gas by being disposed parallel to a flow of the object gas.

34. The carbon monoxide sensor according to claim 26, wherein
said power source is designed such that a voltage thereof ranges from 0.1V to 1.0V.

* * * * *

UNITED STATES PATENT AND TRADEMARK OFFICE
CERTIFICATE OF CORRECTION

PATENT NO. : 6,668,616 B1
DATED : December 30, 2003
INVENTOR(S) : Rihito Shoji et al.

It is certified that error appears in the above-identified patent and that said Letters Patent is hereby corrected as shown below:

Title page,
Item [30], Foreign Application Priority Data, change
"Oct. 1, 1995 (JP) …….. 11-281305" to -- Oct. 1, 1999 (JP) ……… 11-281305 --.
Item [62], Related U.S. Application Data, insert
-- This application is a National Stage application corresponding to PCT/JP00/06740, filed September 29, 2000 --.

Column 1,
Line 2, insert -- This application is a National Stage application corresponding to PCT/JP00/06740, filed September 29, 2000 --.

Signed and Sealed this

Twentieth Day of April, 2004

JON W. DUDAS
*Acting Director of the United States Patent and Trademark Office*